US005663056A

United States Patent [19]
Ollar et al.

[11] Patent Number: 5,663,056
[45] Date of Patent: *Sep. 2, 1997

[54] METHOD FOR DETERMINING THE ANTIMICROBIAL AGENT SENSITIVITY OF A NONPARAFFINOPHILIC MICROORGANISM AND AN ASSOCIATED APPARATUS

[75] Inventors: Robert-A. Ollar, Milford; Mitchell S. Felder, Sharon, both of Pa.

[73] Assignee: Infectech, Inc., Sharon, Pa.

[*] Notice: The portion of the term of this patent subsequent to Nov. 9, 2015, has been disclaimed.

[21] Appl. No.: 528,192

[22] Filed: Sep. 14, 1995

[51] Int. Cl.$^6$ .............................. C12Q 1/02; C12Q 1/04; C12Q 1/24; C12Q 1/18
[52] U.S. Cl. .......................... 435/29; 435/34; 435/4; 435/30; 435/36; 435/42; 435/32; 436/63; 436/74
[58] Field of Search ................... 435/29, 34, 4, 435/30, 36, 42, 32; 436/63, 74

[56] References Cited

U.S. PATENT DOCUMENTS

| | | | |
|---|---|---|---|
| 3,826,717 | 7/1974 | Gilbert et al. | 435/34 |
| 4,683,195 | 7/1987 | Mullis et al. | 435/6 |
| 4,683,201 | 7/1987 | Hamill et al. | 435/6 |
| 4,683,202 | 7/1987 | Mullis | 435/6 |
| 5,153,119 | 10/1992 | Ollar | 435/34 |
| 5,316,918 | 5/1994 | Ollar | 435/34 |

OTHER PUBLICATIONS

Wallace et al., *Chest*, 93 (5) 926–932 (1988) Month Not Available.

Wolinsky, *American Review of Respiratory Disease*, vol. 119: 107–159 (1979) Month Not Available.

Horsburgh, Jr. et al., *Medicine*, vol. 64, No. 1: 36–48 (1983) Month Not Available.

Horsburgh, Jr. et al., *American Review Of Respiratory Disease*, 139:4–7 (1989) Month Not Available.

C.M. Reichert et al., *Aids: Etiology, Diagnosis, Treatment and Prevention*, p. 134, Lippencott (1985) Month Not Available.

C.C. Hawkins et al., *Annals Of Internal Medicine*, 105: pp. 184–188 (1986) Month Not Available.

J. Hoy et al., *The Journal of Infectious Diseases*, 161: 801–805 (1990) Month Not Available.

Fuhs, G.W., *Arch Mikrobiol*, 39: 374–422 (1961) Month Not Available.

Mishra, S.K. et al., *Mycopathologia Et Mycologia Applicata*, vol. 51 (2–3): 147–157 (1973) Month Not Available.

Ollar, *Zbl. Bakt. Hyg. I.Abt. Orig. A 234*: 81–90 (1976) Month Not Available.

Kemper et al., *American Society For Microbiology*, 297 (Abstract) (1990) Month Not Available.

Klatt et al., *Human Pathology*, vol. 18, No. 7: 709–714 (1987) Month Not Available.

Bermudez et al., *The Journal Of Infectious Diseases*, 165: 75–79 (1992) Month Not Available.

Murphy et al., *American Society For Microbiology*, 277 (1983) Month Not Available.

(List continued on next page.)

*Primary Examiner*—Louise Leary
*Attorney, Agent, or Firm*—David V. Radack; Eckert Seamans Cherin & Mellott, LLC

[57] ABSTRACT

A method for determining the sensitivity of at least one nonparaffinophilic microorganism from a specimen obtained from a patient to different antimicrobial agent and predetermined quantities thereof. The method includes providing at least one receptacle containing an aqueous solution and inoculating the solution with the specimen. The method further includes placing into the receptacle (i) a slide coated with a carbon source and (ii) a predetermined quantity of an antimicrobial agent to be tested. By observing the nonparaffinophilic microorganism growth or lack thereof on the slide, it can be determined whether the predetermined quantity of the antimicrobial agent is effective in inhibiting growth of the nonparaffinophilic microorganism on the slide. An associated apparatus is also disclosed.

13 Claims, 1 Drawing Sheet

OTHER PUBLICATIONS

P. Ma et al., *Aids And Infections Of Homosexual Men*, 233–234 (1989) Month Not Available.

Havlik Jr. et al., *The Journal Of Infectious Diseases*, 165: 577–580 (1992) Month Not Available.

Inderlied et al., *Aids Clinical Review*, 165–191 (1990) Month Not Available.

Gonzalez et al., *Diagn. Microbiol. Infect. Dis.*, 8: 69–77 (1987) Month Not Available.

Ollar et al., *Tubercle*, 71, pp. 23–28 (1990) Month Not Available.

Kemper et al., *Annals Of Internal Medicine*, 116: 466–472 (1992) Month Not Available.

Heifets et al., *Antimicrobial Agents And Chemotherapy*, 1298–1301 (1989) Month Not Available.

Hurley et al., *Journal of Clinical Microbiology*, pp. 1582–1587 (1989) Month Not Available.

Kirihara et al., *Journal Of Clinical Microbiology*, pp. 841–845 (1985) Month Not Available.

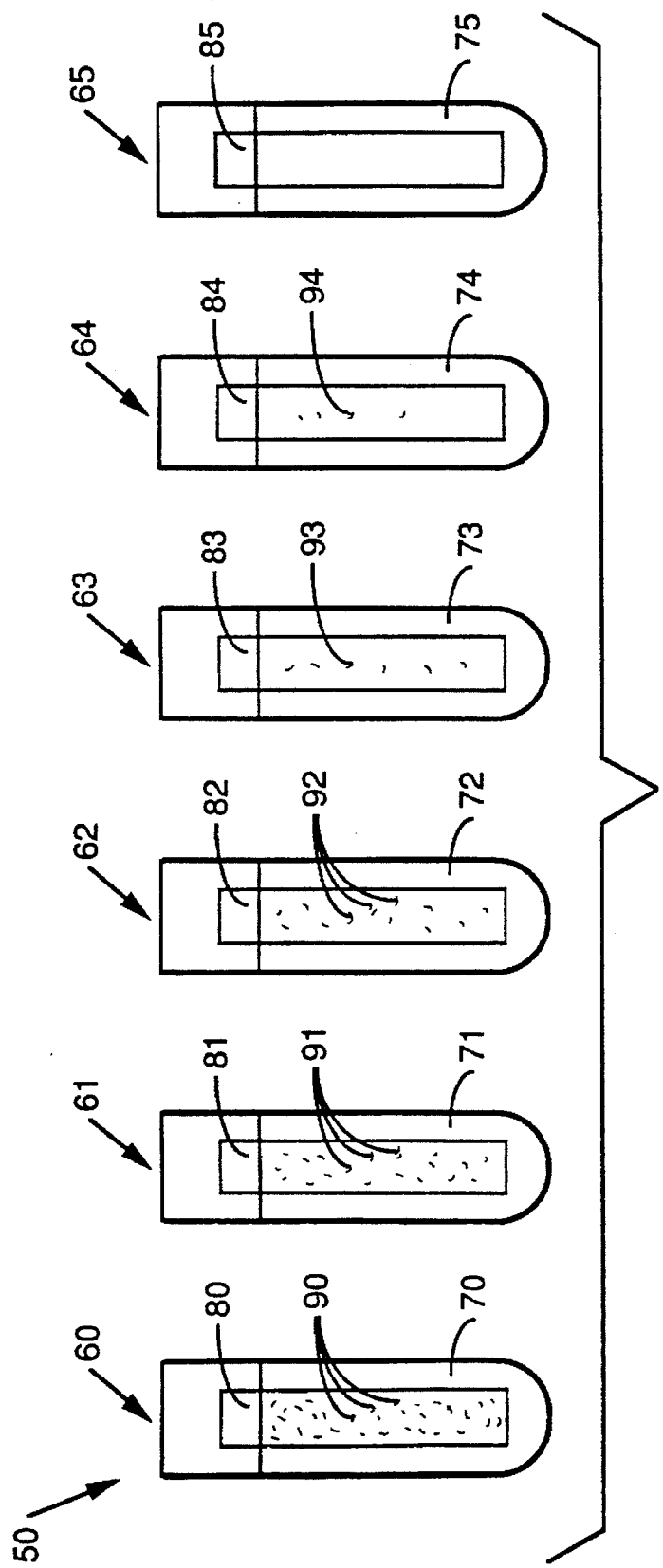

METHOD FOR DETERMINING THE ANTIMICROBIAL AGENT SENSITIVITY OF A NONPARAFFINOPHILIC MICROORGANISM AND AN ASSOCIATED APPARATUS

BACKGROUND OF THE INVENTION

This invention relates to a method for determining the antimicrobial agent sensitivity of a nonparaffinophilic microorganism and an associated apparatus.

Treating infections very often involves educated guesses by medical personnel as to the nature of the microorganism involved and the correct antimicrobial agent and quantity thereof needed to effectively treat the microorganism present in the infected tissue. Often times, there is a need to treat a mixed flora of several microorganisms. Medical personnel are acutely interested in rapidly ascertaining which antimicrobial agents, and which dosages, are necessary in order to assure effective inhibition of the growth of all microorganisms present in the patient.

There is presently no effective, efficient and economical way for a physician to rapidly ascertain which antimicrobial agent, and which dosage is necessary in order to treat the patient. A physician simply does not have available to him or her the type of information regarding antimicrobial agent sensitivity that would make a more exact selection of an antimicrobial agent possible and, once an appropriate antimicrobial agent is selected, facilitate a more precise dosage for treatment. If this information was available, a physician could more effectively treat the infection. Furthermore, because some antimicrobial agents are expensive, the information could be used so that only that amount of antimicrobial agent needed could be used to treat the infection. Finally, and most importantly, as antimicrobial agents can have undesired side effects, the information can be used to find the most effective antimicrobial agent and dosage thereof, which will limit the undesired side effects.

As used herein, the term "nonparaffinophilic microorganism" means any microorganism sustained by a carbon source other than paraffin. Examples of such nonparaffinophilic microorganisms include, but are not limited to, the following: Mycobacterium tuberculosis; Mycobacterium paratuberculosis; Mycobacterium leprae; Staphylococcus; Streptococcus; E. Coli; Listeria; Brucellae; Humemophilus; Treponema; Pneumococcus; Clostridium; Cryptococcus; Coccidioides; and Histoplasma. Also, as used herein, the term "patient" refers to a member of the animal kingdom, including human beings, whose body specimen is being processed by the method and apparatus of the invention.

U.S. Pat. Nos. 5,153,119 and 5,316,918 disclose methods and apparatus for identifying and testing the antibiotic sensitivity of Mycobacterium avium-intracellulare ("MAI"), a paraffinophilic microorganism. The inventor named on those patents is Robert-A. Ollar, one of the co-inventors of the invention disclosed herein. This method involves providing a receptacle containing an aqueous solution and inoculating into the solution a specimen. After this, a paraffin coated slide is placed into the receptacle. The slide is then observed for the presence or absence of growth of MAI.

Despite the existence of Dr. Ollar's patents, there still remains a need for a method of testing the antimicrobial agent sensitivity of one or more nonparaffinophilic microorganisms in a way that maximizes the efficacy of the antimicrobial agent used to inhibit growth of the one or more nonparaffinophilic microorganisms that may be present in a patient.

SUMMARY OF THE INVENTION

The invention has met or exceeded the above-mentioned need as well as others. The method for determining the sensitivity of at least one nonparaffinophilic microorganism from a specimen obtained from a patient to different antimicrobial agent and predetermined quantities thereof comprises providing at least one receptacle containing an aqueous solution and inoculating the solution with the specimen. The method further includes placing into the receptacle (i) a slide coated with a carbon source and (ii) a predetermined quantity of an antimicrobial agent to be tested. By observing the nonparaffinophilic microorganism growth or lack thereof on the slide, it can be determined whether the predetermined quantity of the antimicrobial agent is effective in inhibiting growth of the nonparaffinophilic microorganism on the slide.

An associated apparatus is also disclosed. The apparatus comprises a receptacle adapted to contain an aqueous solution, an amount of antimicrobial agent to be tested and the specimen. The apparatus further includes a slide coated with a carbon source, the slide being adapted to being placed in the receptacle. Again, observation of the growth of the nonparaffinophilic microorganism from the specimen on the slide can be used to determine the concentration of the antimicrobial agent necessary to resist the nonparaffinophilic microorganism growth on the slide.

BRIEF DESCRIPTION OF THE DRAWING

A full understanding of the invention can be gained from the following detailed description of the invention when read in conjunction with the accompanying lone drawing which shows one embodiment of the antimicrobial agent sensitivity apparatus.

DETAILED DESCRIPTION

The method and apparatus of the invention provide an efficient, effective and economical way of determining the sensitivity of at least one nonparaffinophilic microorganism to different antimicrobial agents and predetermined quantities thereof. Referring now to the lone FIGURE, the antimicrobial agent sensitivity method will be explained with reference to one embodiment of the antimicrobial agent sensitivity apparatus 50. The apparatus 50 consists of six receptacles in the form of test tubes 60, 61, 62, 63, 64, 65 each containing an amount of an aqueous solution, such as Czapek broth 70, 71, 72, 73, 74, 75. It will be appreciated that the aqueous solution should not contain any carbon source, as it is desired to provide a sole carbon source on the slide (discussed below) in order to effectively grow the nonparaffinophilic microorganism to be tested on the slide and not in the aqueous solution. The aqueous solutions in test tubes 61–65 contain uniform intervals of increasing concentrations of an antimicrobial agent to be tested. Test tube 60 is used as a control tube that does not contain any antimicrobial agent.

The specimen from the patient is then inoculated into each of the test tubes 60–65. The specimen can be a blood sample; any biopsy or tissue specimen; stomach fluid; urine; cerebral spinal fluid; nasopharyngeal mucosa or saliva. These specimens can be obtained from the patient in the doctor's office or in the emergency room of a hospital, for example, by known techniques.

Slides 80, 81, 82, 83, 84 and 85 coated with a carbon source are then placed into respective test tubes 60, 61, 62, 63, 64 and 65. The slides are incubated for a period of a minimum of twenty-four (24) hours. By observing nonparaffinophilic microorganism growth 90, 91, 92, 93, 94 on the slides 80–85, the minimum inhibitory concentration ("MIC") of the antimicrobial agent necessary to prevent nonparaffinophilic microorganism growth can be determined. In this case, slide 85 has no nonparaffinophilic microorganism growth, thus the MIC concentration is found in test tube 75.

It will be appreciated that a specimen can sometimes have more than one nonparaffinophilic microorganisms present therein. For example, if a patient has a brain abscess associated with a bacterial endocarditis, the patient will most likely have a single pathogen (i.e., staphylococcus). However, there may be a mixed flora which has grown on the slide (i.e., staphylococcus and meningococci). It is imperative, however, to treat all bacterial flora, as any bacteria present are causing pathogenicity in the patient. This invention allows a physician to specify an antimicrobial agent and a particular dosage thereof which will inhibit all flora growing on the slide, and which is thus effective in treating all nonparaffinophilic microorganisms which are causing pathogenicity in the patient.

It will be appreciated that although apparatus 50 is shown with multiple receptacles and multiple slides 80–85, that the invention is not limited to multiple receptacles and multiple slides, but covers also a single receptacle and a single slide.

The carbon source and the slides 80–85 can include a gelatinous matrix containing a carbon source. A carbon source can be one or more of those selected from the group consisting of glucose, fructose, glycenol, mannitol, asparagine and casein, among others. Another embodiment can include providing a slide and coating the slide with an adhesive and securing a plurality of gel beads to the adhesive. The carbon source can then be either ionically or affinity bound to the gel beads.

The slides 80–85 with the gelatinous matrix containing a carbon source can be prepared by the following method. A receptacle, such as a laboratory beaker, is first filled with 100 ml of distilled water. Into the beaker is placed two (2) grams of agar (the gelatinous matrix) and three (3) grams of a carbon source (such as glucose). This mixture is then boiled and steam sterilized and the molten gelatinous matrix with a carbon source is poured into a petri dish, which is sitting on a hot plate. In this way the gelatinous matrix/carbon source remains molten. After this, a sterile slide such as slide 80 is dropped into the molten gelatinous matrix/carbon source and becomes coated therewith. The now coated slide is removed from the petri dish and allowed to stand for a minute or two in order to solidify the coating thereon. The slide with the coating of a gelatinous matrix containing a carbon source is then ready to be placed in one of the test tubes 60–65 containing the aqueous solution and the specimen.

An alternative method of preparing the slide involves first coating the slide with an adhesive, such as collodion and then applying a plurality of gel beads (commercially available from Pharmacia of Parsippany, N.J.) to the adhesive. The gel beads are approximately one micron in diameter. The slide containing the coating of gel beads is now immersed in a buffering agent containing the carbon source (such as glucose) to attach the carbon source to the gel beads either ionically or affinity-wise.

Nonparaffinophilic microorganisms that can be identified using the method of the invention include any microorganism sustained by a carbon source other than paraffin. Nonparaffinophilic microorganisms include, but are not limited to, *Mycobacterium tuberculosis*; *Mycobacterium paratuberculosis*; *Mycobacterium leprae*; Staphylococcus; Streptococcus; *E. Coli*; Listeria; Brucellae; Humemophilus; Treponema; Pneumococcus; Clostridium; Cryptococcus; Coccidioides; and Histoplasma.

It will be appreciated that a method of determining the sensitivity of at least one nonparaffinophilic microorganism in a specimen and an associated apparatus has been disclosed. The method is effective and efficient and does not involve the use of expensive and complicated equipment. An associated apparatus is also disclosed.

While specific embodiments of the invention have been disclosed, it will be appreciated by those skilled in the art that various modifications and alterations to those details could be developed in light of the overall teachings of the disclosure. Accordingly, the particular arrangements disclosed are meant to be illustrative only and not limiting as to the scope of the invention which is to be given the full breadth of the appended claims and any and all equivalents thereof.

What is claimed is:

1. A method for determining the sensitivity of at least one nonparaffinophilic microorganism from a specimen obtained from a patient to different antimicrobial agents and predetermined quantities thereof, said method comprising:

providing at least one receptacle containing an aqueous solution;

inoculating said solution with said specimen;

placing into said receptacle (i) a slide coated with a carbon source and (ii) a predetermined quantity of an antimicrobial agent;

observing said nonparaffinophilic microorganism growth or lack thereof on said slide to determine whether said predetermined quantity of said antimicrobial agent is effective in inhibiting growth of said nonparaffinophilic microorganism on said slide; and employing as said slide one coated with a gelatinous matrix containing said carbon source.

2. The method of claim 1, including employing as said specimen one selected from the group consisting of blood, stomach fluid, urine, cerebral spinal fluid, nasopharyngeal mucosa and saliva.

3. The method of claim 1, including providing a plurality of receptacles each containing an aqueous solution;

inoculating each receptacle with an amount of said specimen;

placing (i) a separate slide and (ii) an amount of an antimicrobial agent to be tested in each receptacle, each said receptacle containing a different predetermined quantity of said antimicrobial agent; and observing said nonparaffinophilic microorganism growth or lack thereof on said slides to determine the minimum inhibitory concentration of said antimicrobial agent to inhibit growth of said nonparaffinophilic microorganism.

4. A method for determining the sensitivity of at least one nonparaffinophilic microorganism from a specimen obtained from a patient to different antimicrobial agents and predetermined quantities thereof, said method comprising:

providing at least one receptacle containing an aqueous solution;

inoculating said solution with said specimen;

placing into said receptacle (i) a slide coated with a carbon source and (ii) a predetermined quantity of an antimicrobial agent;

observing said nonparaffinophilic microorganism growth or lack thereof on said slide to determine whether said predetermined quantity of said antimicrobial agent is effective in inhibiting growth of said nonparaffinophilic microorganism on said slide; and providing said slide by first adhering to said slide a plurality of gel beads and then bonding to said gel beads said carbon source.

5. The method of claim 4, wherein said carbon source is ionically bound to said gel beads.

6. The method of claim 4, wherein said carbon source is affinity bound to said gel beads.

7. The method of claim 4, including adhering said gel beads to said slide by means of an adhesive.

8. The method of claim 7, including employing as said adhesive a gelatinous matrix with said carbon source.

9. The method of claim 4, including employing as said specimen one selected from the group consisting of blood, stomach fluid, urine, cerebral spinal fluid, nasopharyngeal mucosa and saliva.

10. The method of claim 4, including providing a plurality of receptacles each containing an aqueous solution;

inoculating each receptacle with an amount of said specimen;

placing (i) a separate slide and (ii) an amount of an antimicrobial agent to be tested in each receptacle, each said receptacle containing a different predetermined quantity of said antimicrobial agent; and observing said nonparaffinophilic microorganism growth or lack thereof on said slides to determine the minimum inhibitory concentration of said antimicrobial agent to inhibit growth of said nonparaffinophilic microorganism.

11. A method for determining the sensitivity of at least one nonparaffinophilic microorganism from a specimen obtained from a patient to different antimicrobial agents and predetermined quantities thereof, said method comprising:

providing at least one receptacle containing an aqueous solution;

inoculating said solution with said specimen;

placing into said receptacle (i) a slide coated with a carbon source and (ii) a predetermined quantity of an antimicrobial agent;

observing said nonparaffinophilic microorganism growth or lack thereof on said slide to determine whether said predetermined quantity of said antimicrobial agent is effective in inhibiting growth of said nonparaffinophilic microorganism on said slide; and employing as said carbon source one or more of the group consisting of glucose, fructose, glycenol, mannitol, asparagine and casein.

12. The method of claim 11, including employing as said specimen one selected from the group consisting of blood, stomach fluid, urine, cerebral spinal fluid, nasopharyngeal mucosa and saliva.

13. The method of claim 11, including providing a plurality of receptacles each containing an aqueous solution;

inoculating each receptacle with an amount of said specimen;

placing (i) a separate slide and (ii) an amount of an antimicrobial agent to be tested in each receptacle, each said receptacle containing a different predetermined quantity of said antimicrobial agent; and observing said nonparaffinophilic microorganism growth or lack thereof on said slides to determine the minimum inhibitory concentration of said antimicrobial agent to inhibit growth of said nonparaffinophilic microorganism.

\* \* \* \* \*